(12) United States Patent
Loozen et al.

(10) Patent No.: US 6,258,803 B1
(45) Date of Patent: Jul. 10, 2001

(54) C-11 SUBSTITUTED STEROIDS FOR TREATING MENOPAUSAL COMPLAINTS

(75) Inventors: Hubert Jan Jozef Loozen, Uden; Lodewijk Pieter Cornelis Schot; Jane Margretha Lena van der Werf-Pieters, both of Oss, all of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/426,022

(22) Filed: Oct. 25, 1999

Related U.S. Application Data

(62) Continuation of application No. 09/008,178, filed on Jan. 16, 1998, now Pat. No. 6,037,339, which is a division of application No. 08/791,084, filed on Jan. 29, 1997, now Pat. No. 5,710,144, which is a continuation of application No. 08/464,845, filed as application No. PCT/EP94/00348 on Feb. 4, 1994, now abandoned.

(30) Foreign Application Priority Data

Feb. 8, 1993 (EP) .................................................. 93200332

(51) Int. Cl.[7] .................................................. A61K 31/56
(52) U.S. Cl. .......................................................... 514/179
(58) Field of Search ............................................... 514/179

(56) References Cited

U.S. PATENT DOCUMENTS

| 3,325,520 | 6/1967 | Baran et al. . |
|---|---|---|
| 3,465,010 | 9/1969 | Baran et al. . |
| 3,983,144 | 9/1976 | Leemhuis et al . |
| 4,292,251 | 9/1981 | Overbeek . |

FOREIGN PATENT DOCUMENTS

| 3702383 | 8/1988 | (DE) . |
|---|---|---|
| 0136011 | 4/1985 | (EP) . |
| 0145493 | 6/1985 | (EP) . |
| 0337938 | 10/1989 | (EP) . |
| 0461290 | 12/1991 | (EP) . |
| 0474374 | 3/1992 | (EP) . |
| 1190240 | 11/1967 | (GB) . |
| 2058564 | 4/1981 | (GB) . |
| 7216767 | 12/1972 | (NL) . |
| 7701384 | 8/1978 | (NL) . |
| 8502571 | 4/1987 | (NL) . |

OTHER PUBLICATIONS

A.J. van den Broeck et al., *Rec. Trav. Chim. Pays–Bas*, 94:2:35–39, 1975.

J.S. Baran et al., *Experientia*, 26/7:762–763, 1970.

H.O. Hoppen et al., *Acta Endocrinologica*, 115:406–412, 1967.

E.W. Bergink, et al., *Journal of Steroid Biochem*, 14:175–183, 1980.

*Primary Examiner*—Rebecca Cook
(74) *Attorney, Agent, or Firm*—Michael G. Sullivan

(57) ABSTRACT

A C-11 substituted steroid and a method of use of a C-11 substituted steroid to provide an estrogenic effect to a human or animal.

2 Claims, No Drawings

C-11 SUBSTITUTED STEROIDS FOR TREATING MENOPAUSAL COMPLAINTS

This is a continuation of U.S. Ser. No. 09/008,178, filed Jan. 16, 1998, now U.S. Pat. No. 6,037,339, which is a divisional of U.S. Ser. No. 08/791,084, filed Jan. 29, 1997, now U.S. Pat. No. 5,710,144, which is a continuation of U.S. Ser. No. 08/464,845, filed Sep. 26, 1995, now abandoned, which is a U.S. National Phase application of PCT/EP94/00348, filed Feb. 4, 1994.

The invention relates to the use of steroids for the manufacture of a medicament for treating or preventing menopausal complaints, especially for treating or preventing osteoporosis.

Many of the steroids according to this invention, which are used for the treatment of menopausal complaints, are known per se.

For instance, 11β-alkyl steroid are known from U.S. Pat. No. 3,983,144. These steroids are described to have interesting anti-fertility activity. Other 11β-alkyl steroids having anabolic, androgenic, and progestational activity are disclosed in U.S. Pat. No. 3,325,520. Related progestational compounds for menstrual and ovulation control are further known from Australian patent application AL 6614974, European patent application 0,145,493, and U.S. Pat. No. 3,465,010. Steroids having unsaturated hydrocarbon groups at position 11 of the steroid skeleton are known from U.S. Pat. No. 4,292,251, which patent discloses uterotropic and ovulation inhibiting activity, and from above-mentioned EP 0,145,493.

It has now been found that compounds having the general formula:

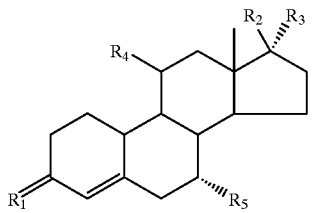

I wherein
- $R_1$ represents O, (H,OH), or two hydrogens atoms;
- $R_2$ is hydroxy, optionally etherified or esterified;
- $R_3$ is (2–6 C) alkynyl, optionally substituted with hydroxy;
- $R_4$ is CN or one of the hydrocarbon groups selected from (1–6 C) alkyl, (1–6 C) alkoxy, (2–6 C) alkenyl, (2–6 C) alkynyl, and (2–6 C) alkylidene, each of said hydrocarbon groups may optionally be substituted with halogen, hydroxy or (1–6 C) alkoxy; and
- $R_5$ is hydrogen or (1–6 C) alkyl, can be used for treating or preventing postmenopausal complaints, and especially osteoporosis.

One of the most serious menopausal complaints is bone loss (osteoporosis), which characteristically affects women. The aim of this invention is to provide a medicament which is able to prevent bone loss, and possibly to increase bone mass, and further to treat climacteric complaints. Preferably the active ingredients of these medicaments have strong estrogen and weak or non-existing androgenic activity. Preferred medicaments further have favourable bleeding properties, do not induce endometrium proliferation, and have a favourable HDL/LDL (high/low density lipid) ratio.

In a preferred embodiment the compounds have the general formula I wherein $R_1$ represents O or two hydrogens atoms; $R_2$ is hydroxy; $R_3$ is ethynyl; $R_4$ is selected from the group consisting of methyl, (2–6 C) alkynyl, (2–6 C) alkylidene, and one of (2–6 C) alkyl, (2–7 C) alkoxy-alkyl, (1–6 C) alkoxy, or (2–6 C) alkenyl, which may optionally be substituted with halogen; and $R_5$ is hydrogen or (1–6 C) alkyl.

More preferred is the use of steroids having the general formula I wherein: $R_1$ is O; $R_2$ is hydroxy; $R_3$ is ethynyl; $R_4$ is ethyl, 2-fluoroethyl, ethynyl, (2–6 C) alkenyl optionally substituted with fluorine, or (2–6 C) alkylidene optionally substituted with fluorine; and $R_5$ is hydrogen or methyl. In the preferred embodiment $R_5$ is hydrogen.

Even more preferred is the use of steroids having the general formula I wherein: $R_1$ is O; $R_2$ is hydroxy; $R_3$ is ethynyl; $R_4$ is ethyl or ethynyl; and $R_5$ is hydrogen.

The invention further relates to new steroids having the general formula I wherein:
- $R_1$ represents O;
- $R_2$ is hydroxy, optionally etherified or esterified;
- $R_3$ is (2–6 C) alkynyl, optionally substituted with hydroxy;
- $R_4$ is CN, (2–6 C) alkyl optionally substituted with halogen, or (2–6 C) alkenyl substituted with halogen; and
- $R_5$ is hydrogen or (1–6 C) alkyl;

or wherein
- $R_1$ represents two hydrogens atoms;
- $R_2$ is hydroxy, optionally etherified or esterified;
- $R_3$ is (2–6 C) alkynyl, optionally substituted with hydroxy;
- $R_4$ is CN or one of the hydrocarbon groups selected from (2–6 C) alkyl, (1–6 C) alkoxy, (2–6 C) alkenyl, (2–6 C) alkynyl, and (2–6 C) alkylidene, each of said hydrocarbon groups may optionally be substituted with halogen, hydroxy or (1–6 C) alkoxy; and
- $R_5$ is (1–6 C) alkyl.

The steroids of general formula I wherein $R_1$ is O; $R_2$ is hydroxy; $R_3$ is ethynyl; $R_4$ is 2-fluoroethyl or 2-fluoroethenyl; and $R_5$ is hydrogen are preferred steroids.

Other preferred steroids are steroids of general formula I wherein $R_1$ represents two hydrogens atoms; $R_2$ is hydroxy; $R_3$ is ethynyl; $R_4$ is (2–6 C) alkyl, (2–6 C) alkylidene or (2–6 C) alkenyl, each of which groups may be substituted with fluorine; and $R_5$ is methyl.

In the definition of $R_2$ the OH group may be etherified or esterified. The term etherified means that the hydroxy group is etherified with a lower alkyl group, preferably having 1–6 carbon atoms, such as methyl, ethyl, propyl, sec-butyl and the like. The term esterified means that the hydroxy group is esterified with a lower alkanoyl group, preferably having 2–6 carbon atoms, like acetyl, propionyl, and the like. In principle any ester suffices as long as the ester group cleaves when the compound is administered in vivo.

The (1–6 C) alkyl group in the definition of formula I is a branched or unbranched alkyl group having 1–6 carbon atoms, such as methyl, ethyl, propyl, butyl, tert-butyl, pentyl and hexyl. Preferably the alkyl group is methyl (especially for $R_5$) and ethyl (especially for $R_4$). The term (2–6 C) alkyl has the same meaning with the exception of methyl.

The (2–6 C) alkenyl group is a branched or unbranched alkenyl group having 2–6 carbon atoms, like vinyl, 2-propenyl, and 1,3-butadienyl.

The (2–6 C) alkynyl group is a branched or unbranched alkynyl group having 2–6 carbon atoms, like ethynyl, propynyl, butynyl, and the like.

The (2–6 C) alkylidene group is a branched or unbranched alkylidene group having 2–6 carbon atoms, like ethylidene, propylidene, 2-methylpropylidene, and the like.

The term halogen used in the definition of formula I means fluorine, chlorine, bromine or iodine. Fluorine is the preferred halogen.

The term (1–6 C) alkoxy means an alkoxy group, the alkyl moiety of which is a (1–6 C) alkyl group as previously defined.

The term (2–7 C) alkoxyalkyl means a (1–6 C) alkyl group as previously defined substituted by a (1–6 C) alkoxy group as previously defined, the total number of carbon atoms being between 2 and 7.

The new compounds of this invention can be prepared by condensation of 11-keto steroids of the general formula:

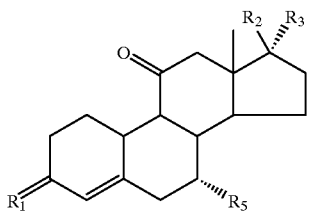

II wherein
  $R_1$ represents O;
  $R_2$ is hydroxy, optionally etherified or esterified;
  $R_3$ is (2–6 C) alkynyl, optionally substituted with hydroxy; and
  $R_5$ is hydrogen or (1–6 C) alkyl;
or wherein
  $R_1$ represents two hydrogens atoms;
  $R_2$ is hydroxy, optionally etherified or esterified;
  $R_3$ is (2–6 C) alkynyl, optionally substituted with hydroxy; and
  $R_5$ is (1–6 C) alkyl;
the active groups of which are optionally protected, is condensed with a Wittig(-like) compound of the formula $R_4'R_4''CH-W$, wherein $R_4'R_4''C$ forms the group $R_4$ which is the optionally halogen, hydroxy, or (1–6 C) alkoxy substituted (2–6 C) alkylidene group as previously defined, or $R_4'''Li$, wherein $R_4'''$ is (2–6 C) alkyl or (2–6 C) alkenyl optionally substituted with halogen, hydroxy, or (1–6 C) alkoxy, in which reactive groups can be protected by protective groups which are known in the art (see for example T. W. Green: Protective Groups in Organic Synthesis, Wiley, N.Y., 1981), and W is a Wittig, Wittig-Horner or Peterson-like moiety, optionally followed by halogenation and dehydration or by hydration, after which the compound obtained is converted into a nitrile or condensed with a Wittig(-like) compound of the formula $R_6W$, wherein W has the previously given meaning and $R_6$ is independently hydrogen, halogen or (1–6 C) alkyl, followed by hydroboration, optionally followed by alkylation, halogenation, or halogenation and dehydrohalogenation, or (partial) hydrogenation, after which optionally present protective groups are removed.

Suitable reagents are triphenylphosphoranes such as $R_4'R_4''CH-P(Hal)Ph_3$ and the like, and suitable Peterson reagents are, for example, trimethylsilane reagents like $R_4'R_4''C(MgHal)Si(CH_3)_3$, wherein Hal denotes a halogen like chlorine or bromine.

The steroids of the invention can be used to prevent and treat estrogen deficiency induced disorders such as menopausal complaints, as is demonstrated in the estrogen-induced bone loss assay. In this assay young mature female Wistar rats are ovariectomized and treated with the test compound for 1 month. After 1 month blood is collected and in the lithium-heparin plasma the bone turnover parameter (osteocalcin) is determined according to the method of Verhaeghe et al., J. Endrocrinol., 120, 143–151. At autopsy the right femur is dissected and the bone density of the distal part of the metaphyse is measured using an X-ray densitometric method. The bone density, in mm aluminum equivalent, is expressed in a percentage relative to the intact control group which is 100% by definition, and to the ovariectomized control group which is 0% by definition.

The value for osteocalcin is defined as 100% for the ovariectomized group and 0% for the intact group. Active compounds inhibit the bone turnover, and thus have an osteocalcin value lower than 100%. Table I gives the results of this assay.

TABLE 1

| $R_1$ | $R_2$ | $R_3$ | $R_4$ | $R_5$ | dose ($\mu$g) | bone density (%) | osteo-calcin (%) |
|---|---|---|---|---|---|---|---|
| reference: | | | | | | | |
| O | OH | C≡CH | H | H | 1000 | 24 | 55 |
| this invention: | | | | | | | |
| O | OH | C≡CH | $C_2H_5$ | H | 64 | 94 | −117 |
| O | OH | C≡CH | $CH_2Cl$ | H | 10 | 57 | −78 |
| O | OH | C≡CH | $CH_2OCH_3$ | H | 250 | 66 | −45 |
| O | OH | C≡CH | $CH=CH_2$ | H | 100 | 48 | −52 |
| O | OH | C≡CH | C≡CH | H | 250 | 115 | −117 |
| O | OH | C≡CH | C≡N | H | 1000 | 113 | −35 |
| O | OH | C≡CH | $CH_{2=CH}$ | $CH_3$ | 1000 | 90 | −80 |
| O | OH | C≡CH | $OCH_3$ | H | 1000 | 73 | −46 |
| O | OH | C≡CH | $CH_3$ | H | 125 | 81 | |
| O | OH | C≡CH | $CH_2CH_2F$ | H | 500 | 93 | −59 |
| O | OH | C≡CH | (E)=CHCH$_3$ | H | 64 | 86 | |
| O | OH | C≡CH | C≡N | H | 125 | 119 | −66 |
| O | OH | C≡CH | $C_2H_5$ | $CH_3$ | 250 | 115 | |
| $H_2$ | OH | C≡CH | $CH_3$ | H | 1000 | 80 | −54 |
| $H_2$ | OH | C≡CH | $CH_2Cl$ | H | 10 | 43 | −72 |
| $H_2$ | OH | C≡CH | $CH_2Cl$ | H | 100 | 81 | −112 |
| $H_2$ | OH | C≡CH | $CH=CH_2$ | $CH_3$ | 1000 | 124 | −80 |
| $H_2$ | OH | C≡CH | C≡CH | H | 32 | 66 | −17 |

The compounds of the invention may be administered enterally or parenterally, and for humans preferably in a daily dosage of 0.001–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

EXAMPLE 1

To a solution of 115 g of (7α,11α)-11-hydroxy-7-methylestr-4-en-3,17-dione in 5 l of acetone were added dropwise at 0.5° C. 110 ml of 8 N chromic acid. After stirring for 1 h 50 ml of propanol-2 were added and 15 min later the mixture was concentrated partially and diluted with 3 l of water. After stirring for several hours, the precipitate was filtered, taken up in a small volume of dichloromethane and dried with sodium sulfate, to give after evaporation of the organic solvent 107 g of triketone (7α)-7-methylestr-4-en-3,11,17-trione. $R_f$=0.54 (toluene-ethyl acetate 4–6 v/v).

A mixture of 115 g of (7α)-7-methylestr-4-en-3,11,17-trione, 8 g of p-toluenesulfonic acid and 40 ml of ethanedithiol in 1 l of absolute ethanol was refluxed for 1 h. After cooling the mixture was diluted with 1 l of water and stirred in the cold for several hours. The precipitate was filtered and washed with 1 N NaOH, water and cold methanol. After drying 134 g of (7α)-3,3-ethanedithio-7-methylestr-4-en-11,17-dione were obtained. $R_f$=0.62 (toluene-ethyl acetate 8/2).

A solution consisting of 36 g of (7α)-3,3-ethanedithio-7-methylestr-4-en-11,17-dione, 300 ml of dichloromethane, 85 ml of triethylorthoformate, 70 ml of ethylene glycol and 2 g of p-toluenesulfonic acid was stirred for 7 h. Then the mixture was washed with 10% sodium carbonate solution and dried, concentrated and passed through a silica gel column to provide 44 g of product (7α)-3,3-ethanedithio-17,17-ethylenedioxy-7-methylestr-4-en. $R_f$=0.65 (toluene-ethyl acetate 8/2).

A mixture of 9.2 g of potassium tert-butoxide, 34.8 g of methyltriphenylphosphonium bromide in 260 ml of toluene was refluxed for 1 h. Then 7.8 g of (7α)-3,3-ethanedithio-17,17-ethylenedioxy-7-methylestr-4-en were added and the mixture was boiled for another 2 h. Then the reaction was cooled, washed with water, dried and concentrated. The residue was chromatographed to give 6.1 g of (7α)-3,3-ethanedithio-17,17-ethylenedioxy-7-methyl-11-methylene-estr-4-en. $R_f$=0.77 (toluene-ethyl acetate 9/1).

A mixture of 6.1 g of (7α)-3,3-ethanedithio-17,17-ethylenedioxy-7-methyl-11-methylene-estr-4-en, 90 ml of acetone, 50 ml of tetrahydrofuran and 3 ml of 6 N hydrochloric acid was stirred at ambient temperature. After 1 h the mixture was diluted by addition of 700 ml of 5% sodium carbonate and stirred for ½ h. The precipitate was filtered and dried to provide 5.4 g of (7α)-3,3-ethanedithio-7-methyl-11-methylene-estr-4-en-17-one. $R_f$=0.74 (toluene-ethyl acetate 9/1).

Acetylene gas was passed through a solution of 50 g of potassium tert-butoxide in 500 ml of dry tetrahydrofuran. After 2 h a solution of 30 g of (7α)-3,3-ethanedithio-7-methyl-11-methylene-estr-4-en-17-one in 400 ml of tetrahydrofuran was introduced dropwise at 0° C. After stirring for an additional 1 h the mixture was poured into 7 l of water and stirred for an additional ½ h. The precipitates were filtered and dried to give 31 g of (7α,17α)-3,3-ethanedithio-17-hydroxy-7-methyl-11-methylene-19-norpregn-4-en-20-yne. $R_f$=0.64 (toluene-ethyl acetate 9/1).

To a solution of 8 g of sodium in 300 ml of liquid ammonia at −50° C. was added dropwise a solution of 16 g of (7α,17α)-3,3-ethanedithio-7-methyl-11-methylene-19-norpregn-4-en-20-yn-17-ol in 75 ml of tetrahydrofuran. After stirring for 1 h, excess sodium was destroyed by addition of 10 ml of ethanol. After evaporation of ammonia, the residue was partioned between dichloromethane and water. The organic layer was separated, washed and dried. The material which left after evaporation of the solvent was chromatographed to provide 5.4 g of (7α,17α)-7-methyl-11-methylene-19-norpregn-4-en-20-yn-17-ol. $R_f$=0.59 (toluene-ethyl acetate 9/1).

EXAMPLE 2

A mixture of 15 g of (7α,17α)-3,3-ethanedithio-7-methyl-11-methylene-19-norpregn-4-en-20-yn-17-ol, 300 ml of methanol, 20 ml of water, 6 g of calcium carbonate and 51 ml of methyl iodide was refluxed for 6 h. After filtration over Hy-flow, the filtrate was concentrated taken up in dichloromethane, washed, dried and evaporated. The remaining residue was chromatographed to provide 6.5 g of (7α,17α)-17-hydroxy-7-methyl-11-methylene-19-norpregn-4-en-20-yn-3-one. $R_f$=0.40 (toluene-ethyl acetate 9/1).

EXAMPLE 3

To a solution of 134 g of (7α)-3,3-ethanedithio-7-methylestr-4-en-11,17-dione in 5 l of dry tetrahydrofuran were added in portions 110 g of lithium tri-tert-butoxy aluminium hydride at 0–5° C. After stirring for 3 h the mixture was poured into 10 l of ice water and acidified slightly by addition of 1 l of 2 N hydrochloric acid. The product was extracted with ethyl acetate. After drying with sodium sulfate the organic material was treated with diethyl ether, to provide 133 g of essentially pure (7α,17β)-3,3-ethanedithio-17-hydroxy-7-methylestr-4-en-11-one. $R_f$=0.45 (toluene-ethyl acetate 6/4).

To a solution of 132 g of (7α,17β)-3,3-ethanedithio-17-hydroxy-7-methylestr-4-en-11-one in 800 ml of pyridine were added at 0° C. 182 ml of trimethylsilyl chloride. After stirring for 1 h the mixture was poured into ice water and the product was extracted with ethyl acetate. After washing, drying and evaporation of the solvent, the residue was co-evaporated with toluene and then treated with hexane to provide 137 g of (7α,17β)-3,3-ethanedithio-7-methyl-17-trimethylsilyloxy-estr-4-en-11-one. $R_f$=0.63 (toluene-ethyl acetate 6/4).

To a suspension of 334 g of methoxymethyltriphenylphosphonium chloride in 6 l of dry ether were added dropwise 600 ml of 1.6 M butyl lithium at 0.5° C. After stirring for 1 h a solution of 44.6 g of (7α,17β)-3,3-ethanedithio-7-methyl-17-trimethylsilyloxy-estr-4-en-11-one in 1.5 l of diethyl ether were added and the mixture was stirred for 24 h. The organic solution was then washed with water and dried. The residue which remained after concentration of the organic phase was partitioned between hexane-methanol-water (1/0.7/0.3 v/v/v), and stirred for 15 min. The hexane phase was dried and concentrated to provide 47 g of (7α,17β)-3,3-ethanedithio-11-methoxymethylene-7-methyl-17-trimethylsilyloxy-estr-4-en. $R_f$=0.50 (hexane-ethyl acetate 3/1).

To a solution of 265 g of (7α,17β)-3,3-ethanedithio-11-methoxymethylene-7-methyl-17-trimethylsilyloxy-estr-4-en in 800 ml of acetone were added 80 ml of concentrated hydrochloric acid and the mixture was stirred at room temperature. After 1 h the mixture was poured into water and extracted with ethyl acetate. After washing, drying and evaporation of the organic solvent, the remaining residue was passed through a silica gel column and eluted with dichloromethane-acetone 9/1 to provide 63 g of (7α,11β,17β)-3,3-ethanedithio-17-hydroxy-7-methyl-estr-4-en-11-carboxaldehyde. $R_f$=0.38 (toluene-ethyl acetate 7/3).

To a solution of 55 g of (7α,11β,17β)-3,3-ethanedithio-17-hydroxy-7-methylestr-4-en-11-carboxaldehyde and 165 ml of dihydropyrane in 1100 ml of dry tetrahydrofuran were added 1.3 g of p-toluenesulfonic acid. After stirring for 2 h the mixture was poured into 5 l of 5% sodium hydrogencarbonate solution and the product was extracted with ethyl acetate. After concentration of the organic phase (7α,11β, 17β)-3,3-ethanedithio-17-tetrahydropyranyloxy-7-methylestr-4-en-11-carboxaldehyde was isolated.

A mixture of 1 g of (7α,11β,17β)-3,3-ethanedithio-17-tetrahydropyranyloxy-7-methylestr-4-en-11-carboxaldehyde and 2 g of hydroxylamine hydrochloride in 12 ml of pyridine was stirred at 80° C. for 1 h. Then it was cooled, poured into water and extracted with ethyl acetate. After washing, drying and concentration 0.9 g of amorphous (7α,11β,17β)-3,3-ethanedithio-17-tetrahydropyranyloxy-7-methylestr-4-en-11-carboxaldehyde oxime were obtained. $R_f$=0.60 (toluene-ethyl acetate 8/2).

Dehydration of the oxime was effected by reacting 0.8 g of (7α,11β,17β)-3,3-ethanedithio-17-tetrahydropyranyloxy-7-methylestr-4-en-11-carboxaldehyde oxime in 8 ml of acetic anhydride during 45 min. Concomitant replacement of the 17-tetrahydropyran ether by an acetate group was observed. The reaction mixture was poured into 50 ml of ice water and stirred for 30 min. After neutralization with 2 N sodium hydroxide and extraction with ethyl acetate 0.75 g of (7α,11β,17β)-3,3-ethanedithio-17-acetyloxy-7-methylestr-4-en-11-carbonitrile was obtained. $R_f$=0.58 (toluene-ethyl acetate 9/1).

The acetate functionality was saponified by stirring 0.75 g of (7α,11β,17β)-3,3-ethanedithio-17-acetyloxy-7-methylestr-4-en-11-carbonitrile for 30 min in a mixture of 20 ml of tetrahydrofuran and 10 ml of water containing 1 g of sodium hydroxide. The mixture was diluted and extracted with ethyl acetate. After drying and evaporation 0.50 g of (7α,11β,17β)-3,3-ethanedithio-17-hydroxy-7-methylestr-4-en-11-carbonitrile was obtained. $R_f$=0.34 (toluene-ethyl acetate 9/1).

To a solution of 20 g of (7α,11β,17β)-3,3-ethanedithio-17-hydroxy-7-methylestr-4-en-11-carbonitrile in 600 ml of dry dichloromethane were added 20 g of sodium acetate, followed by 85 g of pyridinium chlorochromate. After stirring for 3 h the reaction turned out to be complete. Excess oxidant was removed by addition of 40 ml of propanol-2. The mixture was filtered over Hy-Flow, concentrated and chromatographed to provide 13 g of (7α,11β)-3,3-ethanedithio-17-keto-7-methylestr-4-en11-carbonitrile. $R_f$=0.75 (toluene-ethyl acetate 8/2).

Acetylene gas was passed through a solution of 10.5 g of potassium tert-butoxide in 60 ml of dry tetrahydrofuran for 1 h at 0° C. Then a solution of 9.3 g of (7α,11β)-3,3-ethanedithio-17-oxo-7-methylestr-4-en-11-carbonitrile in 100 ml of tetrahydrofuran were added dropwise. After stirring for 1 h at 0–5° C. the mixture was poured into 500 ml of saturated ammonium chloride solution and the product was extracted with ethyl acetate. After washing, drying and concentration 9.5 g of (7α,11β,17α)-3,3-ethanedithio-17-hydroxy-7-methyl-19-norpregn-4-en-20-yne-1-carbonitril was obtained. $R_f$=0.28 (toluene-ethyl acetate 9/1).

A mixture of 6.5 g of (7α,11β,17α)-3,3-ethanedithio-17-hydroxy-7-methyl-19-norpregn-4-en-20-yne-11-carbonitrile, 200 ml of methanol, 100 ml of tetrahydrofuran, 2.4 g of calcium carbonate, 8.5 ml of water, and 35 ml of methanol was refluxed for several hours, additional methanol was added from time to time and after disappearance of starting material the mixture was cooled, filtered and concentrated. The residue was passed through a silica column and provided 2.5 g of pure (7α,11β,17α)-17-hydroxy-7-methyl-3-oxo-19-norpregn-4-en-20-yne-11-carbonitrile. M.p. 234° C. $R_f$=0.33 (toluene-ethyl acetate 7/3).

EXAMPLE 4

Hydroboration of the 11-methylene function in 3,3,17,17-bis(ethylenedioxy)-11-methylene-estr-5-en was accomplished as follows:

To a solution of 2.18 ml of 10 M boron hydride-dimethylsulfoxide complex in 10 ml of dry tetrahydrofuran were added at 0° C. 2.7 ml of cyclo-octadiene. After additional reflux for 1 h a solution of 2.7 g of 3,3,17,17-bis(ethylenedioxy)-11-methylene-estr-5-en in 30 ml of tetrahydrofuran were added. The mixture was stirred for 16 h and then treated with 10 ml of 10% sodium hydroxide, followed by 10 ml of 30% hydrogen peroxide. After stirring for an additional 4 h the mixture was poured into water and the product extracted with dichloromethane. Final purification was achieved by chromatography to provide 2 g of (11β)-3,3,17,17-bis(ethylenedioxy)-11-(hydroxymethyl)-estr-5-en. $R_f$=0.25 (toluene-ethyl acetate 1/1).

To a suspension of 20 g of pyridinium chlorochromate in 200 ml of dichloromethane were added 9.3 g of (11β)-3,3,17,17-bis(ethylenedioxy)-11-(hydroxymethyl)-estr-5-en in 100 ml of dichloromethane. After stirring for 1 h, excess oxidant was destroyed by addition of 40 g of sodium hydrogensulfite in 200 ml of water, followed by extraction of the product with ethyl acetate. After drying and concentration of the organic phase the residue was purified by chromatography to provide 5.4 g of (11β)-3,3,17,17-bis(ethylenedioxy)-estr-5-en-11-carboxaldehyde. $R_f$=0.50 (hexane-ethyl acetate 1/1).

A solution of 1.6 M butyl lithium in hexane (44 ml) was added dropwise to a suspension of 24.4 g of chloromethyl-triphenylphosphonium chloride in 500 ml of ether. After stirring for 15 min a solution of 5.4 g of (11β)-3,3,17,17-bis(ethylenedioxy)-estr-5-en-11-carboxaldehyde in 30 ml of tetrahydrofuran were added dropwise. After 12 h the mixture was poured into 0.5 l of water and the organic phase was separated, washed, dried and concentrated. The residue was chromatographed to provide 3.7 g of E/Z (11β)-3,3,17,17-bis(ethylenedioxy)-11-(2-chloroethenyl)-estr-5-en. $R_f$=0.4 (hexane-ethyl acetate 7/3).

To a suspension of lithium amide, prepared from 920 mg of lithium in 130 ml of ammonia (liq.), were added at –45° C. a solution of 3.6 g of (11β)-3,3,17,17-bis(ethylenedioxy)-11-(2-chloroethenyl)-estr-5-en in 30 ml of tetrahydrofuran. After stirring for 1 h the excess reagent was destroyed by addition of 15 g of ammonium chloride, followed by evaporation of ammonia. The residue was partioned between dichloromethane and water; the organic phase was dried and concentrated and chromatographed to provide 1.8 g of (11β)-3,3,17,17-bis(ethylenedioxy)-11-ethynyl-estr-5-en; M.p. 200° C. $R_f$=0.45 (hexane-ethyl acetate 7/3).

A mixture of 8 g of (11β)-3,3,17,17-bis(ethylenedioxy)-11-ethynyl-estr-5-en, 200 ml of acetone, 100 ml of methanol and 100 ml of tetrahydrofuran was treated with 5 ml of 6 N hydrochloric acid and stirred overnight. After treatment with sodium hydrogencarbonate and concentration, the residue was chromatographed to give 5.1 g of (11β)-11-ethynyl-estr-4-en-3,17-dione. $R_f$32 0.48 (hexane-ethyl acetate 1/1).

A mixture of 2.7 g of potassium tert-butoxide in 12 ml of tetrahydrofuran and 5 ml of tert-butanol was placed under nitrogen and acetylene gas was bubbled through for 1.5 h at 0° C. Then a suspension of 1.85 g of (11β)-11-ethynyl-estr-4-en-3,17-dione in 5 ml of tetrahydrofuran was introduced, and stirring was prolonged for 1 h. The mixture was diluted with water (200 ml), neutralized by addition of 2 N hydrochloric acid and extracted with ethyl acetate, dried and concentrated. The residue was chromatographed to provide 1.6 g of (11β,17α)-11-ethynyl-17-hydroxy-19-norpregn-4-en-20-yn-3-one; M.p. 168° C. $R_f$=0.60 (hexane-ethyl acetate 1/1).

EXAMPLE 5

To a solution of 4 ml of borane methylsulfide (10M in tetrahydrofuran) in 20 ml of tetrahydrofuran were added dropwise 5 ml of 1,5-cyclo-octadiene. After stirring for 1 h a solution of 5 g of 11β-vinyl-3,3,17,17-bisethylenedioxy-estr-5-ene (obtained by selective Lindlar hydrogenation from (11β)-3,3,17,17-bis(ethylenedioxy)-11-ethynyl-estr-5-en) in 25 ml of tetrahydrofuran was added dropwise. After stirring for an additional hour 20 ml of 15% aq sodium hydroxide and 20 ml of 30% hydrogen peroxide were added. After stirring overnight the product was extracted with ethyl acetate and the organic material thus obtained was purified by chromatography to give 3.4 g of 11β-(2-hydroxyethyl)-3,3,17,17-bisethylenedioxy-estr-5-ene; M.p. 190° C.

To a solution of 5 g of 11β-(2-hydroxyethyl)-3,3,17,17-bisethylenedioxyestr-5-ene in 7 ml of tetrahydrofuran were added at −30° C. 500 mg of 2,6-di-t-butylpyridine followed by 800 mg of trifluoromethanesulfonic anhydride. After stirring for an additional 15 min at −30° C., 10 ml of a 1M solution of tetrabutylammonium fluoride in tetrahydrofuran were added and the mixture was stirred for 2 h at room temperature and then poured into 30 ml of 10% sodium hydrogencarbonate solution. Then the mixture was extracted with ethyl acetate and the organic material was purified by chromatography to give 600 mg of 11β-(2-fluoroethyl)-3,3,17,17-bisethylenedioxy-estr-5-ene; M.p. 196° C.

To a solution of 580 mg of 11β-(2-fluoroethyl)-3,3,17,17-bisethylenedioxy-estr-5-ene in a mixture of 3 ml of acetone and 3 ml of tetrahydrofuran were added 6 ml of 3M hydrochloric acid. After stirring for 2 h sodium hydrogen-carbonate and water were added and the product was extracted with ethyl acetate. The residue obtained after evaporation of the solvent was treated with diisopropyl ether to give 400 mg of 11β-(2-fluoroethyl)-estr-4-en-3,17-dione; M.p. 85° C.

Acetylene gas was passed into a solution of 0.7 g of potassium tert-butoxide in 5 ml of tetrahydrofuran and 1 ml of tert-butanol. After 15 min a solution of 400 mg of 11β-(2-fluoroethyl)-estr-4-en-3,17-dione in 5 ml of tetrahydrofuran was added. After stirring for an additional 15 min the solution was poured into water and the product was extracted with ethyl acetate. The organic material thus isolated was purified by column chromatography and treated with ether, to provide 320 mg of (11β,17α)-11-(2-fluoroethyl)-17-hydroxy-19-norpregn-4-ene-20-yn-3-one; M.p. 212° C.

EXAMPLE 6

To a solution of lithium diisopropylamide (prepared from 250 mg of diisopropylamine and 1.6 ml of a 1.6M butyl lithium-hexane solution) in 3 ml of tetrahydrofuran was added a solution of 600 mg of difluoromethyldiphenylphos-phinoxide in 2 ml of tetrahydrofuran at −50° C. After stirring for 15 min a solution of 800 mg of (11β)-3,3,17,17-bis-(ethylenedioxy)-estr-5-en-11-carboxaldehyde in 3 ml of tetrahydrofuran was added and the mixture was stirred overnight at room temperature. The reaction products were poured into water and extracted with ethyl acetate. Chromatography of the organic material provided 465 mg of 11β-(2,2-difluoroethenyl)-3,3,17,17-bis-(ethylenedioxy)-estr-5-en; M.p. 180–181° C.

A solution of 430 mg of above-mentioned product in a mixture of 3 ml of acetone and 2 ml of tetrahydrofuran was treated with 2 ml of 4N hydrochloric acid. After stirring for 2 h the mixture was neutralized with solid sodium hydro-gencarbonate and the product was extracted with ethyl acetate. The organic material thus obtained was crystallised from diisopropyl ether to provide 270 mg of 11β-(2,2-difluoroethylene)-estr-4-en-3,17-dione; M.p. 150° C.

Acetylene gas was bubbled into a solution of 0.48 g of potassium tert-butoxide in a mixture of 5 ml of tetrahydrofuran and 0.5 ml of t-butanol. After 15 min a solution of 250 mg of 11β-(2,2-difluoroethylene)-estr-4-en-3,17-dione in 3 ml of tetrahydrofuran was added and 15 min later the mixture was quenched with water and the product extracted with ethyl acetate.

The organic material thus isolated was treated with diisopropyl ether to provide 160 mg of (11β,17α)-11-(2,2-difluoroethenyl)-17-hydroxy-19-norpregn-4-ene-20-yn-3-one; M.p. 196° C.

EXAMPLE 7

A mixture of E/Z 11β,3,3,17,17-bis-(ethylenedioxy)-11-(2-chloroethenyl)-estr-4-en was separated on a silica column to provide the pure E-isomer (m.p. 143° C.) and the Z-isomer (m.p. 182° C.). Treatment of a solution of 3 g of (E)11β,3,3,17,17-bis-(ethylenedioxy)-11-(2-chloroethenyl)-estr-5-en in 20 ml of acetone with 3 ml of conc. hydrochloric acid during 1 h followed by neutralization with sodium hydrogencarbonate solution and ethyl acetate extraction provided the desired diketone (11β,E)-11-(2-chloroethenyl)-estr-4-ene-3,17-dione (2.3 g).

This product was dissolved in 10 ml of tetrahydrofuran and added dropwise to a solution of potassium acetylide in a mixture of 14 ml of tetrahydrofuran and 3 ml of tert-butanol (potassium acetylide was generated by passing acetylene gas into a solution of 2.9 g of potassium tert-butoxide in above-mentioned t-butanol-tetrahydrofuran mixture). After stirring for ½ h the mixture was quenched with water and the product was extracted with ethyl acetate. The organic material was purified by chromatography to provide 1.9 g of (11β,E,17α)-11-(2-chloroethenyl-17-hydroxy-19-norpregn-4-ene-20-yn-3-one; M.p. 180° C.

EXAMPLE 8

Similarly as above-described were prepared:

| $R_1$ | $R_2$ | $R_3$ | $R_4$ | $R_5$ | M.p.(° C.) |
|---|---|---|---|---|---|
| O | OH | C≡CH | $C_2H_5$ | H | 217 |
| O | OH | C≡CH | (E)CHCH$_3$ | H | 213 |
| O | OH | C≡CH | C≡CH | $CH_3$ | 268 |
| O | OH | C≡CH | (E)CHC$_4$H$_9$ | $CH_3$ | 230 |
| O | OH | C≡CH | $C_2H_5$ | $CH_3$ | 222 |
| O | OH | C≡CH | $CH_3$ | $CH_3$ | 219 |
| O | OH | C≡CH | CN | $CH_3$ | 234 |
| O | OH | C≡CH | $CH_2OCH_3$ | $CH_3$ | amorphous |
| O | OH | C≡CH | $CH_3$ | H | 221 |
| O | OH | C≡CH | C≡CH | H | 165 |
| O | OH | C≡CH | CH=CH$_2$ | $CH_3$ | 223 |
| O | OH | C≡CH | CN | H | 208 |
| O | OH | C≡CH | CH=C(CH$_3$)$_2$ | H | 212 |
| O | OH | C≡CH | (Z)CH=CHF | H | 215 |
| O | OH | C≡CH | CH$_2$CH$_2$F | $CH_3$ | 151 |
| O | OH | C≡CH | n-C$_3$H$_7$ | H | 208 |
| O | OH | C≡CH | CH=CF$_2$ | $CH_3$ | 169 |
| O | OH | C≡CH | (E)CH=CHCH$_3$ | H | 168 |
| O | OH | C≡CH | (Z)CH=CHCH$_3$ | H | 169 |
| O | OH | C≡CH | (E)—CH—CH$_3$ | $CH_3$ | 235 |
| O | OH | C≡CH | CH$_2$CH$_2$F | H | 212 |
| O | OH | C≡CH | CH=CF$_2$ | H | 196 |
| O | OH | C≡CH | (E)CH=CHCl | H | 180 |
| O | OH | C≡CH | (Z)CH=CHCl | H | 186 |
| O | OH | C≡CH | (E)—CH—CH$_2$F | H | |
| O | OH | C≡CH | (E)—CH—CH$_2$F | $CH_3$ | |
| $H_2$ | OH | C≡CH | C≡CH | $CH_3$ | 116 |
| $H_2$ | OH | C≡CH | (E)CHC$_4$H$_9$ | $CH_3$ | 120 |
| $H_2$ | OH | C≡CH | CN | $CH_3$ | 172 |

-continued

| R₁ | R₂ | R₃ | R₄ | R₅ | M.p.(° C.) |
|---|---|---|---|---|---|
| H₂ | OH | C≡CH | C₂H₅ | CH₃ | 120 |
| H₂ | OH | C≡CH | CH₃ | CH₃ | 119 |
| H₂ | OH | C≡CH | CH₂OCH₃ | CH₃ | 134 |
| H₂ | OH | C≡CH | CH₃ | H | 107 |
| H₂ | OH | C≡CH | C≡CH | H | 98 |
| H₂ | OH | C≡CH | C=CH₂ | CH₃ | 135 |
| βOH | OH | C≡CH | (E)CHCH₃ | H | 145 |
| βOH | OH | C≡CH | (E)CHC₄H₉ | H | 172 |
| βOH | OH | C≡CH | C≡CH | CH₃ | 217 |
| βOH | OH | C≡CH | C₂H₅ | CH₃ | 133 |
| βOH | OH | C≡CH | CH₃ | CH₃ | 151 |
| βOH | OH | C≡CH | CN | CH₃ | 243 |
| βOH | OH | C≡CH | CH₃ | H | 183 |
| βOH | OH | C≡CH | CH₂OCH₃ | CH₃ | amorphous |
| βOH | OH | C≡CH | CH₂ | CH₃ | 194 |
| βOH | OH | C≡CH | CH=C(CH₃)₂ | H | 164 |
| βOH | OH | C≡CH | (Z)CH=CHF | H | 79 |
| βOH | OH | C≡CH | CH₂CH₂F | CH₃ | 185 |
| βOH | OH | C≡CH | n-C₃H₇ | H | 109 |
| βOH | OH | C≡CH | CH=CF₂ | CH₃ | 158 |
| βOH | OH | C≡CH | (E)CH=CHCH₃ | H | 112 |
| βOH | OH | C≡CH | (Z)CH=CHCH₃ | H | 90 |
| βOH | OH | C≡CH | (E)=CH—CH₃ | CH₃ | 124 |
| βOH | OH | C≡CH | CH₂CH₂F | H | 95 |
| βOH | OH | C≡CH | CH=CF₂ | H | 135 |
| βOH | OH | C≡CH | (E)CH=CHCl | H | amorphous |
| βOH | OH | C≡CH | (Z)CH=CHCl | H | amorphous |
| βOH | OH | C≡CH | (E)=CH—CH₂F | H |  |
| βOH | OH | C≡CH | (E)=CH—CH₂F | CH₃ |  |

EXAMPLE 9

A tablet having the following composition was prepared:

| | |
|---|---|
| (11β,17α)-17-hydroxy-11-ethyl-19-norpregn-4-en-20-yn-3-one | 2.5 mg |
| starch | 10 mg |
| ascorbyl palmitate | 0.2 mg |
| magnesium stearate | 0.5 mg |
| lactose | to make up to 100 mg |

Base granules were prepared by mixing the lactose with a portion of starch. The remainder of the starch was mixed to a slurry with water and added to the mixture. The whole was granulated and dried. These base granules were mixed with ascorbyl palmitate and the active ingredient, sieved, finely mixed with magnesium stearate and then tabletted.

EXAMPLE 10

A tablet having the same composition as in Example 9 was prepared with (11β,17α)-11-ethynyl-17-hydroxy-19-norpregn-4-en-20-yn-3-one as active ingredient.

EXAMPLE 11

A tablet having the same composition as in Example 9 was prepared with (7α,11β,17α)-11-methylene-17-hydroxy-7-methyl-19-norpregn-4-en-20-yn as active ingredient, by first mixing the active ingredient with 10% of the lactose and the ascorbyl palmitate and then mixing this mixture with the lactose, starch and starch slurry. The mixture was dried, finely mixed with magnesium stearate and tabletted.

EXAMPLE 12

A capsule having the following composition was prepared:

| | |
|---|---|
| (11β,17α)-11-ethyl-17-hydroxy-19-norpregn-4-en-20-yn-3-one | 2.5 mg |
| starch | 10 mg |
| ascorbyl palmitate | 0.2 mg |
| magnesium stearate | 0.5 mg |
| Avicel | to make up to 100 mg |

The components were mixed with one another in the manner described in Example 9, granulated and filled into gelatin capsules.

What is claimed is:

1. A pharmaceutical composition comprising a pharmaceutically effective amount of (11β,17α)-11-ethyl-17-hydroxy-19-norpregn-4-en-20-yn-3-one and a pharmaceutically acceptable auxiliary.

2. A method for providing an estrogenic effect to a human or animal, comprising administering to said human or animal an effective amount of (11β,17α)-11-ethyl-17-hydroxy-19-norpregn-4-en-20-yn-3-one.

* * * * *